(12) United States Patent
Laning

(10) Patent No.: US 10,376,554 B1
(45) Date of Patent: *Aug. 13, 2019

(54) COMPOSITION AND METHOD FOR TREATING A HANGOVER

(71) Applicant: George Jordan Laning, San Diego, CA (US)

(72) Inventor: George Jordan Laning, San Diego, CA (US)

(73) Assignee: George Jordan Laning, San Diego, CA (US)

( * ) Notice: Subject to any disclaimer, the term of this patent is extended or adjusted under 35 U.S.C. 154(b) by 229 days.

This patent is subject to a terminal disclaimer.

(21) Appl. No.: 15/469,574

(22) Filed: Mar. 27, 2017

Related U.S. Application Data

(63) Continuation-in-part of application No. 14/283,594, filed on May 21, 2014, now Pat. No. 9,603,886, which is a continuation-in-part of application No. 13/310,684, filed on Dec. 2, 2011, now abandoned.

(60) Provisional application No. 61/458,972, filed on Dec. 3, 2010.

(51) Int. Cl.
| | |
|---|---|
| *A61K 36/8962* | (2006.01) |
| *A61K 36/42* | (2006.01) |
| *A61K 9/14* | (2006.01) |
| *A61K 9/08* | (2006.01) |
| *A61K 9/00* | (2006.01) |
| *A61K 36/28* | (2006.01) |
| *A23L 23/00* | (2016.01) |
| *A23L 33/00* | (2016.01) |

(52) U.S. Cl.
CPC .......... *A61K 36/8962* (2013.01); *A23L 23/00* (2016.08); *A23L 33/30* (2016.08); *A61K 9/0053* (2013.01); *A61K 9/08* (2013.01); *A61K 9/14* (2013.01); *A61K 36/28* (2013.01); *A61K 36/42* (2013.01); *A23V 2002/00* (2013.01)

(58) Field of Classification Search
USPC ..... 426/2, 615, 648, 518, 519, 521; 424/757
See application file for complete search history.

(56) References Cited

U.S. PATENT DOCUMENTS

| | | | |
|---|---|---|---|
| 4,006,219 A | 2/1977 | Upham et al. | |
| 4,165,376 A | 8/1979 | Rosenberg | |
| 4,594,249 A | 6/1986 | Procter et al. | |
| 5,712,309 A * | 1/1998 | Finnin .................. | A61K 9/0007 514/562 |

(Continued)

FOREIGN PATENT DOCUMENTS

WO    WO01209125 A1 *  9/2011

OTHER PUBLICATIONS

George Washington University, Health Promotion and Prevention Services, Colonial Health Center, "Alcohol Absorption," http://prevention.gwu.edu/alcohol-absorption.

(Continued)

*Primary Examiner* — Nina Bhat

(57) ABSTRACT

A powdered or liquid juice product for hangover treatment containing juiced ingredients of red onion, cucumber, and romaine lettuce. Other embodiments contain onion, cucumber, and one or more of any other leafy green vegetable. The components of the applicant's invention create a novel synergistic effect because the combination creates a greater effect than the sum of the effects of the components separately.

26 Claims, 10 Drawing Sheets

(56) References Cited

U.S. PATENT DOCUMENTS

| | | | |
|---|---|---|---|
| 7,037,532 B2* | 5/2006 | Foxman | A61K 9/2086 424/725 |
| 8,507,015 B2 | 8/2013 | Thorsby et al. | |
| 9,603,886 B1* | 3/2017 | Laning | A61K 36/8962 |
| 10,022,399 B1* | 7/2018 | Force | A61K 33/24 |
| 2003/0018063 A1* | 1/2003 | Zenovich | A21D 2/08 514/440 |
| 2004/0082667 A1* | 4/2004 | McCadden | A61K 31/10 514/709 |
| 2006/0045929 A1 | 3/2006 | Lee | |
| 2006/0112584 A1 | 6/2006 | Jones | |
| 2006/0222682 A1* | 10/2006 | Andrews | A61K 36/185 424/439 |
| 2006/0233774 A1* | 10/2006 | Lim | A23L 2/52 424/93.45 |
| 2008/0075710 A1* | 3/2008 | Cornett | A61K 31/025 424/94.63 |
| 2008/0299284 A1* | 12/2008 | Jang | A23F 3/34 426/597 |
| 2010/0183736 A1* | 7/2010 | Hays | A61K 36/258 424/602 |
| 2011/0052735 A1 | 3/2011 | Wiesche et al. | |
| 2011/0280977 A1* | 11/2011 | Park | A23L 2/52 424/765 |
| 2014/0314887 A1* | 10/2014 | Paek | A61K 36/72 424/765 |
| 2016/0353777 A1* | 12/2016 | Gillespie | C12G 3/00 |

OTHER PUBLICATIONS

Loyola Marymount University, "Blood Alcohol Content," http://academics.lmu.edu/headsup/forstudents/bloodalcoholcontent/.

Barbara Bates, FitDay, "Alkaline vs. Acidic Foods: What This Means to You," http://www.fitday.com/fitness-articles/fitness/alkaline-vs-acidic-foods---what-this-means-to-you.ht.

"A list of Acid / Alkaline Forming Foods," http://www.rense.com/1.mpicons/acidalka.htm.

Altered States, "Monitoring your Body's PH levels," http://altered-states.net/barry/update178/.

Jerry R. Balentine, Do, Facep , "Alcohol Intoxication Causes," http://www.emedicinehealth.com/alcohol_intoxication/page3_em.htm.

Virtual Medical Center, "Alcohol Hangovers," Jan. 21, 2011 (Modified: Sep. 29, 2015), http://www.myvmc.com/lifestyles/alcohol-hangovers/.

SELF Nutrition Data, http://nutritiondata.self.com/facts/vegetables-and-vegetable-products/2475/2.

"Which foods are acidic?" Columbia Health, Sep. 12, 2003, pp. 1-3, goaskalice.columbia.edu/which-foods-are-acidic.

Du Toit, Alexandra, "10 Health Benefits of Cucumbers," Natural News, Aug. 11, 2012, pp. 1-9, www.naturalnews.com/036769_cucumbers_health_benefits_rehydration.html#.

Filiponne, "Cure-Bananas," About.com Guide, Jan. 1, 2005, p. 1, http://homecooking.about.com/b/2005/01/hangover-cure-bananas.htm.

Buddy T, "The Cures and Remedies for Hangovers," About.com Guide, pp. 1 and 2, Nov. 25, 2010, http://alcoholism.about.com/od/hangovers/a/cures/htm.

Krishan, Shubhra, "16 Superb Health Benefits of Cucumber," Care 2 Healthy Living, Jun. 13, 2013, pp. 1-8, www.care2.com/greenliving/16-superb-health-benefits-of-cucumber.html.

"Cirrhosis" MedlinePlus, Dec. 23, 2010, www.nlm.nih.govmedlineplus/cirrhosis.html.

"Folate Deficiency Anemia," New York Presbyterian Hospital, Nov. 30, 2008, nyp.org/health/blood-folate.html.

Reviewed by Kimball Johnson, MD., "What is Gastritis?" WebMD, Jul. 7, 2012, pp. 1-2, WebMD, LLC.

Raisbeck, Aurora, "Health Benefits of Onions," Foods-Healing-Power.com, pp. 1-12, www.foods-healing-power.com/health-benefits-of-onions.html.

"Cucumber, with Peel, Raw," SELF Nutrition Data, pp. 1-4 nutritiondata.self.com/fact/vegetables-and-vegetable-products/2439/2.

"Lettuce, Cos or Romaine, Raw," SELF Nutrition Data, pp. 1-4, nutritiondata.self.com/facts/vegetables-and-vegetabe-products/2475/2.

"Turnip Greens, Cooked, Boiled, Drained, without Salt," SELF Nutrition Data, pp. 1-4, nutritiondata.self.com/facts/vegetables-and-vegetable-products/2704/2.

Spray Drying Systems, Inc., "Spray Dryers and Spray Drying Technology," www.spraydrysys.com/spray-dryers/spray-dryers.htm.

Boatman Marking, "What are Vacuum Sealers and How do they work?" www.boatmanmarking.com/what_are_vacuum_sealers_and_How_do_they_work-10000007.aspx.

EatByDate, LLC., "How long Does Lettuce Last?" www.eatbydate.com/vegetables/fresh-vegetables/how-long-does-lettuce-last/.

EatByDate, LLC., "How long Does Lettuce Last?" https://www.eatbydate.com/vegetables/fresh-vegetables/how-long-do-cucmbers-last-shelf-life-expiration-date/.

National Onion Association, "Frequently Asked Questions," https://www.onions-usa.org/faqs.

* cited by examiner 10        12            15

| Name | Age | Sex | Average Drinks Consumed in a night | Severity of Hangover* | Results After 5 Minutes | Results After 1 Hour | Results After 2 Hours | Results After 4 Hours |
|---|---|---|---|---|---|---|---|---|
| Jason | 29 | M | 6 | 6 | Improved | No hangover | No hangover | No hangover |
| Stephanie | 24 | F | 10 | 6 | Improved | Improved | Same | No hangover |
| Grady | 25 | M | 16 | 8 | Improved | Improved | Improved | No hangover |
| Derek | 30 | M | 10+ | 4 | Improved | Improved | Improved | No hangover |
| Anna | 30 | F | 6 | 6 | Improved | Same | Improved | No hangover |
| Christine | 29 | F | 5 | 4 | Same | Improved | Improved | No hangover |
| Nate | 28 | M | 8 | 5 | Same | Same | Improved | No hangover |
| Jeffrey | 37 | M | 4-8 | 5 | Same | Same | Improved | No hangover |
| Roxanne | 29 | F | 8 | 6 | Same | Improved | Improved | Improved, No hangover after 6 hours |
| Amanda | 33 | F | 10 | 10 | Same | Improved | Improved | Improved to a Severity of 3 |

*Severity of hangover is rated on a scale of 1 to 10, with 1 being least hung-over and 10 being most hung-over

42

COMPOSITION AND METHOD FOR TREATING A HANGOVER

CROSS-REFERENCE TO RELATED APPLICATIONS

This application is a continuation-in-part application of U.S. patent application Ser. No. 14/283,594, filed May 21, 2014, which is a continuation-in-part application of U.S. patent application Ser. No. 13/310,684, filed Dec. 2, 2011 (now abandoned), which claims the benefit of Provisional Application No. 61/458,972, filed Dec. 3, 2010, which applications are incorporated here in their entirety by this reference.

BACKGROUND OF THE INVENTION

Hangover is the generic term for the ailments associated with alcohol related sickness. These ailments include weak stomach, vomiting, upset stomach, acidic stomach, nausea, dehydration, elevated body temperature, rapid heart rate, heart palpitations, difficulty concentrating, bloodshot eyes, trouble sleeping, depression, anxiety, irritability, sensitivity to light and noise, blurred vision, dizziness, cold sweats, muscular weakness, fatigue, muscle aches, general pain, labored breathing, erratic motor functions, headache, and inability to digest water into the hydration process. In the past hangovers were treated by using pain medicines, but these medicines caused stomach bleeding and only helped to reduce headaches.

Thereafter, several types of hangover remedies have been produced coming in many different forms. These remedies come in pill form, as an effervescent drink additive, and as a health tea. All of these attempts to remedy a hangover contain various vitamins, minerals, and chemicals to combat the symptoms. These methods give inconsistent results due to the unregulated intake of these vitamins, minerals, and chemicals by the human body. Excess amounts of certain vitamins, minerals, and chemicals also bring about unwanted side effects and imbalances in the body's chemistry.

The method for producing known products can also be long and time consuming, making them difficult and costly to streamline for production. The method taught in U.S. Patent Publication No. 2008/0299284 (hereinafter Jang's health tea) involves slicing vegetables and drying them in the sun. This manual operation takes days to complete. This process of production is also heavily impacted by weather and season. The time wasted is costly for the producer who must consider labor, overhead, and production capacity into their business plan.

Some pills, drink additives, and health teas are a combination of many multiple elements which makes them more costly and difficult to produce. For example, Jang's health tea does not contain all the necessary ingredients to completely remedy a hangover. Instead, Jang's health tea uses a list of 14 different elements in combination to create the product. A reduction in unnecessary elements is a reduction in costs to labor, materials, and manufacturing overhead. Useless elements are wasteful and do not add benefits to the product.

A lack of vitamins and minerals can also be a problem associated with these approaches. For example, Jang's health tea contains minute quantities of vitamins and minerals and is focused more on the soothing aspects of hot water which lacks effectiveness in remedying a hangover. The health tea comforts the hung-over individual without effectively treating the symptoms to eradicate them. It is well known that 4, 8, 12, or 16 ounces of liquid tea prepared from tea bags contain a small amount of nutrients as compared to 4, 8, 12, or 16 ounces of a juice from fruits or vegetables, respectively.

Serious side-effects can also be a problem associated with these approaches. Jang's health tea contains ginkgo leaves which when consumed in excess can be toxic as described in the detailed description section of Jang's invention. Jang's health tea contains *Ganoderma lucidum* which when consumed in excess can cause adverse effects as explained in the detailed description section of Jang's invention. Jang's health tea contains roots of sprout beans and *Hedysarum* which can both, when consumed in excess, adversely affect the body of a person who has weak kidney function as described in the detailed description section of Jang's invention. Weak kidney function is common in alcoholic drinkers and can lead to wide spread adverse effects among users of the health tea. Jang's health tea contains *Maximowiczia typica* which when consumed in excess can cause excessive sweating and adverse effects as described in the detailed description section of Jang's invention. The side-effects of some hangover treatments can be dangerous and counterproductive for users, especially when those users are already feeling the adverse effects of an alcoholic hangover.

Seasonality can also be a problem associated with these approaches. Some fruits and vegetables used in hangover treatments are seasonal and are in short supply during the off season months of the year. This makes it difficult and expensive to meet the needs of demand year round. For example, Jang's health tea has a component of persimmons which is seasonal. Persimmons are in season from approximately October to February every year in the United States. The rest of the year persimmons are in short supply. This effectively reduces the production of Jang's health tea during the time period between March and September. Alcohol consumption is year round and the seasonality of some hangover treatments can lead to shortages of those treatments. Shortages of some hangover treatments can cause problems for drinkers that rely on those hangover treatments for their hangover needs.

The present invention is a successful solution to a long-felt, long-existing, and unsolved need since alcohol was discovered. It has been perceived to be insolvable. Hangovers are a worldwide pandemic affecting all humans that consume enough alcohol to induce a hangover. It is a problem for modern society that has not been given a solution until the creation of the present invention.

Humans have tried for a long time to come up with a remedy for hangover symptoms, but none have been successful in properly treating an individual once hangover symptoms are present. All other hangover remedies have only been useful for soothing or masking a hangover but none have been able to eliminate hangover symptoms within a span of 4 hours. For example, Jang's health tea has 14 components and is only used to reduce intoxication of individuals before and during drinking liquor. Jang's health tea is used to reduce the effects of alcohol at the time of consumption of alcohol and prevent alcohol intoxication by consumption of the health tea before drinking the alcohol. Jang's health tea is not meant for the purpose of hangover treatment once hangover symptoms become present, normally occurring the following day after drinking alcohol.

Therefore, there is a great need for a treatment that can quickly alleviate a hangover after onset.

BRIEF SUMMARY OF THE INVENTION

The present invention is a composition comprising three key components and may be used to eliminate hangover symptoms of individuals the day after drinking alcohol when the hangover symptoms have taken effect. The composition comprises a combination of onion, cucumber, and a leafy green vegetable. In some embodiments, the composition is administered in the form of a juice.

In some embodiments, the composition is provided in the form of a powder. Preferably, the powder can be reconstituted in a liquid, such as water, juice, soup, and the like for ease of consumption.

The components of the present invention create a novel synergistic effect because the combination creates a greater effect than the effects of the components separately.

Since a hangover normally occurs the day after an individual has been drinking alcohol and the symptoms present themselves once that individual is no longer intoxicated, present invention is useful because it treats an individual who is suffering from already-present hangover symptoms. The present invention is meant to help individuals who are no longer intoxicated, but are still feeling the effects of a hangover.

In accordance with one embodiment, a hangover treatment comprises cucumber juice, red onion juice, and romaine lettuce juice served fresh for consumption or processed for storage. In accordance with a second embodiment, a hangover treatment comprises spray dried cucumber juice, spray dried red onion juice, and spray dried romaine lettuce juice which is to be added to a liquid, preferably broth, and most preferably chicken broth, then consumed immediately or heated for consumption.

Accordingly several advantages of one or more aspects of the first embodiment of the juice are as follows: to treat more ailments of a hangover; to allow the body to process a safe and naturally regulated amount of vitamins, minerals, and chemicals through natural juice consumption; and to provide sufficient vitamins, minerals, and chemicals to effectively treat hangover symptoms. Also, the present invention provides a hangover remedy that is: produced quickly, mass-manufactured with relative ease, produced with less time and effort, produced without reliance on weather, consumable immediately at the moment of need without preparation, producible year round with readily available components that are not limited by a seasonal availability, and made from natural ingredients that are safe for consumption. Other advantages of one or more aspects will be apparent from a consideration of the drawings and ensuing description.

Accordingly several advantages of one or more aspects of the powder form are as follows: to treat more ailments of a hangover; and to provide sufficient vitamins, minerals, and chemicals to effectively treat hangover symptoms. Also, applicant's invention provides a hangover remedy that is: produced quickly, mass-manufactured with relative ease, produced with less time and effort, produced without reliance on weather, has a longer shelf life, takes up less shelf space in a retail store, has a relatively low shipping and transportation cost due to a minimized weight and size, does not require refrigeration, is packaged easily within small portable containers, is producible year round with readily available components that are not limited by a seasonal availability, and made from natural ingredients that are safe for consumption.

BRIEF DESCRIPTION OF THE DRAWINGS

FIG. 8 shows a table of a study of the effectiveness of the composition and method of the hangover treatment.

DETAILED DESCRIPTION OF THE INVENTION

The detailed description set forth below in connection with the appended drawings is intended as a description of presently-preferred embodiments of the invention and is not intended to represent the only forms in which the present invention may be constructed and/or utilized. The description sets forth the functions and the sequence of steps for manufacturing and using the invention in connection with the illustrated embodiments. However, it is to be understood that the same or equivalent functions and sequences may be accomplished by different embodiments that are also intended to be encompassed within the spirit and scope of the invention. All amounts and concentrations for the composition are approximations to account for manufacturing tolerances and variations that may arise from different manufacturers.

The components of the present invention produce a new and unexpected result because when combined, they do more than their usual function individually. Red onion alone does not alleviate the symptoms of a hangover; cucumber alone does not alleviate the symptoms of a hangover; and romaine lettuce, butterhead lettuce, oakleaf lettuce, turnip greens, or spinach alone do not alleviate the symptoms of a hangover. However, the combination of the proper amount and concentration of red onion, cucumber, and a leafy green vegetable is able to alleviate the symptoms of hangover. These components can be combined as a juice or presented in powder form for reconstitution in a liquid.

The features of the present invention differ from the above references because an effective composition can be achieved using only 3 ingredients. In addition, the present invention differs from the above references because the composition can be manufactured from a juice taken directly from the vegetables which can optionally be spray dried into a powder. Juice that has been dried into a powder will be referred to as juiced powder. For example, onion that has been juiced, then dried into a powder will be referred to as onion juiced powder. Cucumber that has been juiced, then dried into a powder will be referred to as cucumber juiced powder. Green leafy vegetables that have been juiced, then dried into a powder will be referred to as green leafy vegetable juiced powder.

Figure 1:
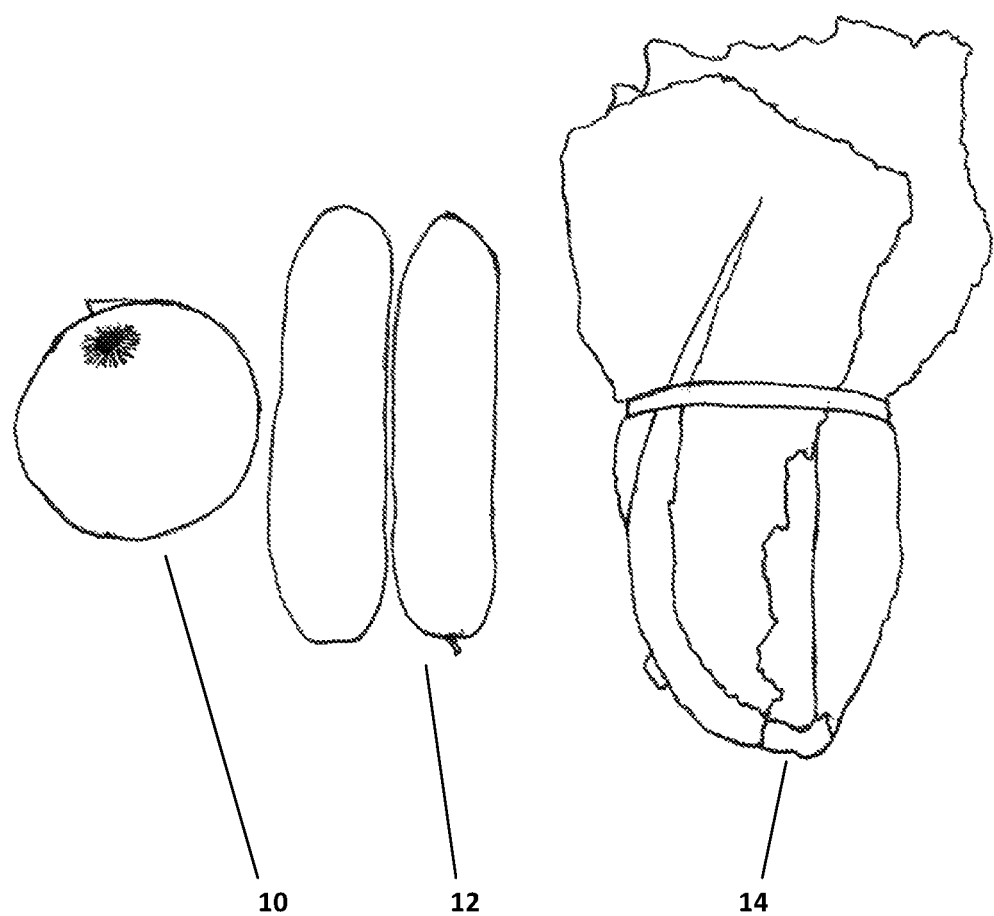
FIG. 1 shows raw elements for one embodiment of the composition for a hangover treatment.

The composition for hangover treatment comprises onion 10, cucumber 12, and a leafy green vegetable. Preferably, the onion is red onion. Preferably, the leafy green vegetable is romaine lettuce 14. FIG. 1 shows raw elements for the preferred embodiment of the hangover treatment. These three components are all that is required in the amounts described herein to alleviate the symptoms of hangover. As such, in one embodiment, the composition for alleviating a hangover may consist essentially of red onion, cucumber, and a leafy green vegetable. Preferably, the leafy green vegetable is romaine lettuce.

However, to create other embodiments of the hangover treatment, romaine lettuce 14 as shown in FIG. 1 can be substituted with one or more of another leafy green vegetables, such as butterhead lettuce 15, oakleaf lettuce 16, turnip greens 17, or spinach 18. Spinach-free or spinach-less leafy greens, specifically, leafy green vegetables other than spinach, may be substituted for leafy green vegetables to avoid health concerns regarding a spinach intolerance or spinach allergy of the consumer.

In addition, other components may be added to improve preservation, consistency, flavoring, and the like. For example, flavorings for new embodiments such as pineapple juice, agave syrup, cayenne pepper, pepper, spices, and sweeteners, may be added to an embodiment and may change with market preferences and after ongoing market research.

The amount of solid, unprocessed red onion 10, cucumber 12, and leafy green vegetable that is required to be consumed is too much for most individuals to eat raw because of its flavor and harsh nature. An individual will likely have to eat approximately 1.5 to approximately 4 ounces of red onions (chopped and with the roots removed), approximately 4 to approximately 11 ounces of cucumbers (peeled and sliced), and approximately 4 to approximately 9 ounces of leafy green vegetables (washed and shredded into edible sized pieces) to consume the effective amount for treating a hangover. Thus it is very likely that if an individual were to try to eat the effective amount of red onion, the individual would probably not be able to and would likely throw up. The other ingredients in their solid form that must be consumed to treat the hangover are also difficult for a hung-over individual to consume because of the nature of their illness which makes consumption of solid foods difficult. A hung-over individual would have difficulty eating the ingredients in their solid form since they would probably be too sick to ingest the composition.

The amount of the hangover treatment necessary to treat hangover symptoms is at least 2 to 4 ounces of juice or one-quarter ounce to one-half ounce of powder. More juice or powder is necessary for hangovers of greater intensities and more doses may be required for lingering hangovers. The average effective hangover treatment is between 5 and 20 ounces of juice or one-quarter ounce to 4 ounces of powder. Preferably, users are likely to drink 5 to 15 ounces of juice or use one-quarter ounce to 3 ounces of powder. Most preferably 8 to 12 ounces of juice or one-half ounce to 2.4 ounces of powder.

In the juice composition of the present invention, red onion juice may be present in an amount ranging from approximately 5 percent to approximately 30 percent of the total weight of the composition. Preferably, the red onion juice is present at approximately 10 percent to approximately 25 percent. Most preferably, the red onion juice is present at approximately 15 percent of the total weight of the composition.

In the powdered composition in which the juice is dried into a powder, the same amounts recited above can be used in juiced powder form of the red onion.

If the total weight of the juice or powder contains less than 5 percent red onion juice or red onion juiced powder the mixture will not be effective because the drink or powder will not cleanse the body. If the total weight of the juice or powder contains more than 30 percent red onion juice or red onion juiced powder the flavor will be too harsh, the mixture will be very difficult to consume, and the mixture may induce vomiting.

Cucumber juice may be present in an amount ranging from approximately 15 percent to approximately 80 percent of the total weight of the juice composition. Preferably, the cucumber juice is present at approximately 30 percent to approximately 70 percent of the total weight of the juice composition. Most preferably, the cucumber juice is present at approximately 52.5 percent of the total weight of the juiced composition.

In the powdered composition, the same amounts recited above can be used in juiced powder form of the cucumber.

If the total weight of the cucumber juice or cucumber juiced powder is less than 15 percent of the total weight of the mixture, the drink will not be effective because the acid in the stomach will not be neutralized or subside. If the total weight of the cucumber juice or cucumber juiced powder is more than 80 percent of the total weight of the mixture the drink will contain either too little leafy green vegetable juice or leafy green vegetable juiced powder or too little red onion juice or red onion juiced powder to be effective.

Leafy green vegetable juice may be present in an amount ranging from approximately 15 percent to approximately 80 percent of the total weight of the juice composition. Preferably, the leafy green vegetable juice is present at approximately 20 percent to approximately 60 percent of the total weight of the composition. Most preferably, the leafy green vegetable juice or leafy green vegetable juiced powder is present at approximately 32.5 percent of the total weight of the composition.

In the powdered composition, the same amounts recited above can be used for in juiced powder form of the leafy green vegetable.

If the total weight of the juice or powder is less than 15 percent leafy green vegetable juice or leafy green vegetable juiced powder, the mixture will not be effective because the juice or powder will lack the necessary vitamins and nutrients. If the total weight of the mixture is more than 80 percent leafy green vegetable juice or leafy green vegetable juiced powder, the drink will contain either too little red onion juice or red onion juiced powder or too little cucumber juice or cucumber juiced powder to be effective.

By way of example only, when including a flavoring such as pineapple juice, the composition for treating a hangover comprises onion juice or onion juiced powder present in an amount ranging from approximately 5 percent to approximately 30 percent of the total weight of the composition, cucumber juice present in an amount ranging from approximately 15 percent to approximately 79 percent of the total weight of the composition, leafy green vegetable juice present in an amount ranging from approximately 15 percent to approximately 79 percent of the total weight of the composition, and pineapple juice present in an amount ranging from approximately 1 percent to approximately 40 percent of the total weight of the composition. The same amounts for each component can be used in the powder form.

Preferably, the red onion juice is present at approximately 10 percent to approximately 25 percent of the total weight of the juice. Preferably, the cucumber juice is present at approximately 30 percent to approximately 70 percent of the total weight of the juice. Preferably, the leafy green vegetable juice is present at approximately 20 percent to approximately 60 percent of the total weight of the juice. Preferably, the pineapple juice is present at approximately 3 percent to approximately 25 percent of the total weight of the juice.

Most preferably, the red onion juice is present at approximately 14 percent of the total weight of the juice. Most preferably, the cucumber juice is present at approximately 47 percent of the total weight of the juice. Most preferably, the leafy green vegetable juice is present at approximately 30 percent of the total weight of the juice. Most preferably, the pineapple juice is present at approximately 9 percent of the total weight of the juice. The same amounts for each component can be used in the powder form.

If the total weight of the juice contains less than 1 percent pineapple juice the drink will not have an improved flavor.

Figure 6:
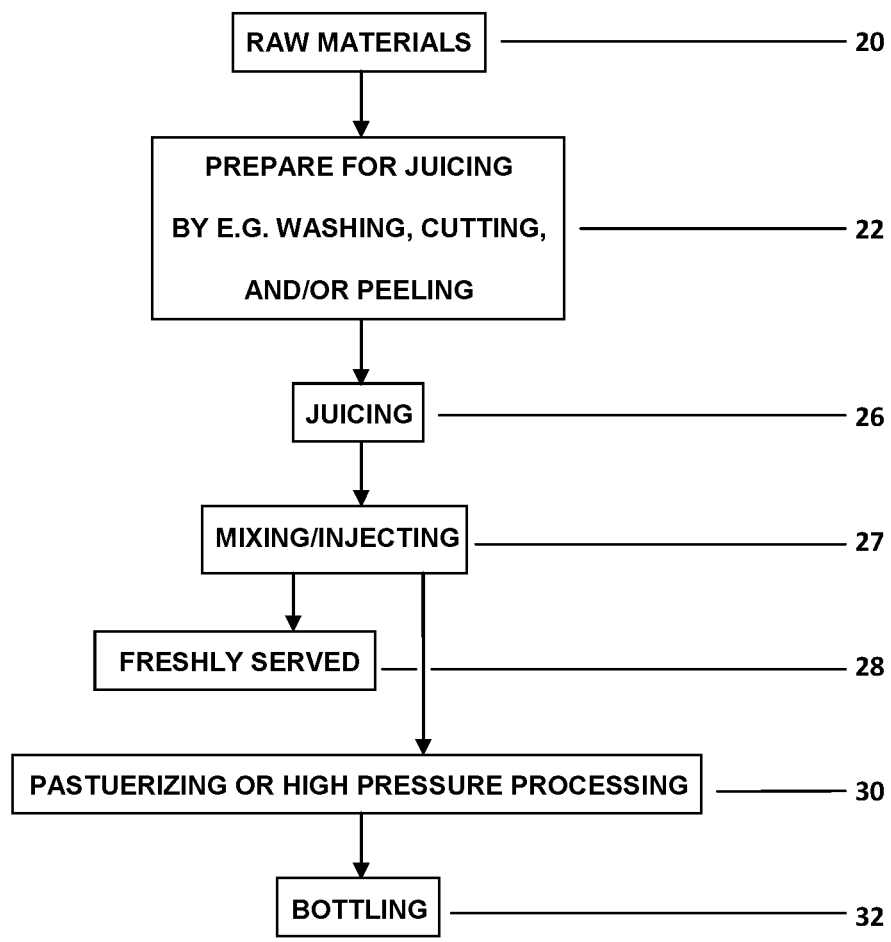
FIG. 6 shows a flow diagram of one embodiment of the procedure for preparing a composition for a hangover treatment.
Figure 7:
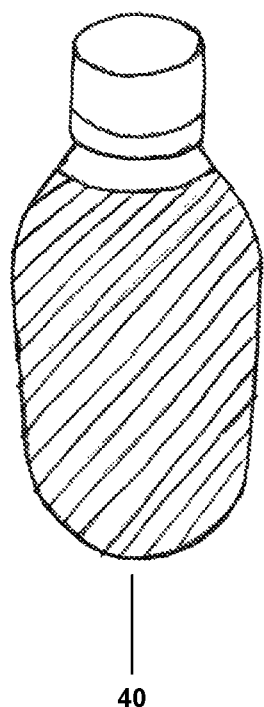
FIG. 7 is an embodiment of a final juice product containing a composition for a hangover treatment.
Figure 9:
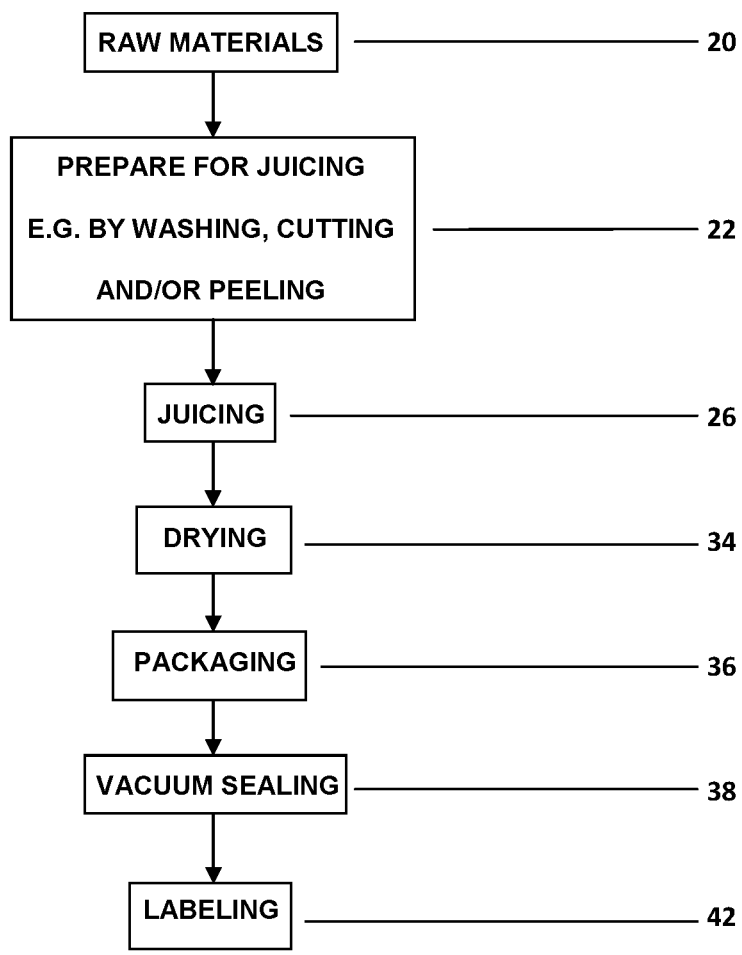
FIG. 9 shows a flow diagram of a second embodiment of the procedure for preparing a composition of the hangover treatment.

The process for making the juice 40 of the present invention is shown in FIG. 6 and FIG. 9. This process involves collecting red onions 10, cucumbers 12, and leafy green vegetables as raw materials 20. The collected raw materials 20 may be prepared for juicing 22 by, for example, washing the vegetable, cutting the vegetable, peeling the vegetable, and the like. For example, each of the raw materials 20 may be washed, red onion 10 may be chopped, and cucumbers 12 may be peeled in preparation for juicing. Juicing is the process of extracting the liquid from a fruit or vegetable from the solid portion, by any means, such as using a juicer. A juicer is a device or machine that separates the liquid portion of a fruit or vegetable from the solid portion (e.g. pulp), for example, with the use of a strainer, filter, press, grinder, blender, or other device. Although some pulp may end up with the liquid portion, the intent is to create a juice. The cucumbers may be peeled to extract the light green flesh, which contains the medicinal properties. The roots of the onion may be chopped off because it does not contain juice and may contain dirt and bacteria. However, any ingredient may be added whole if the juicer has the capability and capacity.

In some embodiments, all prepared ingredients are juiced 26 separately to create separate juice products. In FIG. 6, the juiced compositions are then mixed/injected 27 together to create a juice composition containing the amounts of each component as described above. Preferably, juiced composition is freshly served 28 to treat a hangover. However, the juice may be pasteurized or undergo high pressure processing 30, so that the juice is treated to kill bacteria and can be bottled 32 and stored for distribution. High pressure processing is preferable because it keeps more nutrients in the juice and can extend the shelf life longer than pasteurization can. In bottling 32, the product may be bottled and labeled.

As shown in FIG. 9, the juiced products may be further dried to create a vegetable juiced powder, i.e. vegetables that have been juiced, then dried into a powdered composition. Preferably, the components are juiced and dried separately using, for example, a spray dryer to create powders of each individual component. Spray drying 34 is the preferred method of producing a dry powder from a liquid by rapidly drying with a hot gas. A spray dryer is a device for drying, utilizing a spray, which mixes a heated gas with an atomized (sprayed) liquid stream within a vessel (drying chamber) to accomplish evaporation and produce a free flowing dry powder with a controlled average particle size. The unit operation of spray drying includes the key components of a method of atomizing a solution or slurry, an air/gas heater or a source of hot air, a gas/spray mixing chamber with adequate residence time and droplet trajectory distance for achieving the heat and mass transfer, a means for recovering the solids from the gas stream, and a fan to induce the required air/gas through the spray drying system. Other drying techniques can also be used, such as air drying, vacuum drying, and the like.

In packaging 36, each powder may be made separately, then combined, for example, mixed, admixed, blended, injected together, and the like, to create a powdered composition containing approximately 5 to approximately 30 percent red onion juiced powder, approximately 15 to approximately 80 percent leafy green vegetable juiced powder, and approximately 15 to approximately 80 percent cucumber juiced powder, by weight. These different powders may be mixed and packaged directly into individual plastic, foil, metal, glass, or any other suitable containers for storage. The powders may be combined into these individual packages from separate collection containers of the individual powder. The powders may be injected or poured separately into each individual packing container at the proper percentages to maximize the consistency of the percentage weight of each powder ingredient in each individual container. In some embodiments, the juice may be in the proper concentration and spray dried to create a powder form in the proper concentration without having to mix different powders together.

In Vacuum Sealing 38, each plastic, foil, metal, or glass container may be vacuum packed using a bag heat sealer and air compressor to remove air from the package prior to sealing. By way of example only, a vacuum sealer is a type of bag heat sealer which may be used. The vacuum sealer may be connected to the air compressor so that a vacuum can be drawn. The air compressor may be used to blow air through the sealing equipment. The compressed air passes through a metal tube, which is connected to the contents portion of the bag or container. The compressed air then draws the air from the bag or container out by a method known as the venture effect. When the air has been removed from the bag or container, a heat sealing bar closes around the bag or container, leaving the bag or container sealed.

In Labeling 42, the bag or container is labeled and ready for distribution or direct sale.

Without being bound by theory, it is believed that red onion 10 causes the excretion of alcohol from the body which reduces alcohol levels in the blood. Red onion 10 may also flush out the digestive system which contains the byproducts of drinking, lessening the body's intake of harmful chemicals and reducing stress on the liver and kidneys. Because of this flush of the digestive system, red onion 10 may promote hunger as the digestive system regains normal functioning and processing. Red onion 10 may also contain a powerful antioxidant which helps to thin the blood and lower cholesterol and can help reduce high blood pressure and help heart function. Red onion 10 may help heart function by boosting beneficial HDL cholesterol, thinning the blood, retarding blood clotting, lowering total blood cholesterol, lowering triglycerides, and lowering blood pressure. Red onion 10 may also ward off blood clots and fight infections which can prevent and heal the damage caused by internal bleeding due to heavy drinking. Red onion 10 may also act as an anti-inflammatory, antibiotic, and antiviral, and is thought to have diverse anti-cancer powers, all of which can help the body recover from the damaging effects of drinking alcohol. The antibiotic properties of red onion 10 may help to destroy many disease-causing pathogens in the stomach including *E. coli* and *Salmonella* which may have been ingested during a night of drinking. The diverse anti-cancer powers of red onion 10 may come from the antioxidants in the red onion 10 which can protect against cancer by reducing the DNA damage in cells caused by free radicals. This cancer prevention effect may be helpful in preventing any further damage to the liver and may be helpful for the prevention of liver cancer. Red onion 10 may also cleanse one's blood, body, and skin due to sulfur-containing amino acids found in onions that are able to detoxify one's body from heavy metals such as mercury, cadmium, and lead which are present in alcoholic beverages. This detoxification is important during a hang-over because of the poisoning effect that heavy metals have on the body. Red onion 10 may also contain a significant amount of sulfur, which is good for the liver. The liver is heavily affected by the consumption of alcohol and the sulfur found in red onion 10 can help promote normal liver function.

Without being bound by theory, cucumber 12 is believed to reduce the acidity of the stomach and coat the stomach and intestines to soothe. This may reduce stomach pain, vomiting, and headaches while allowing for the digestive system to recover. After eating cucumber which is highly-alkaline, one's stomach and intestines may regain a normal level of acidity, reducing stomach bleeding and pain. Cucumber 12 may also be an antacid and help relieve heartburn, which is commonly experienced during an alcoholic hangover. Cucumber 12 may also dissolve kidney stones, which can develop due to chronic alcohol consumption. Cucumber 12 may also stabilize the body's blood pressure. It has been found that patients with high or low blood pressure gain relief from eating cucumber 10. This blood pressure stabilization effect may help to reduce the abnormal blood pressure caused by drinking, which is experienced during an alcoholic hangover. Cucumber 10 may also lower uric acid levels in one's system, which helps to keep one's kidneys healthy. Kidneys are negatively affected by drinking, and cucumber 10 can help to reduce those negative effects experienced during a hangover. Cucumber 10 may also reduce bad cholesterol. This reduction of bad cholesterol in the body promotes healthy heart function. Cucumber 10 may also provide a very good source of vitamin K, which can prevent cirrhosis of the liver by preventing vitamin K deficiency-induced bleeding in the intestines and liver. Vitamin K deficiency can be caused by drinking alcohol in excess amounts and can lead to vitamin K deficiency-induced bleeding in the intestines and liver while an individual is hung-over. Cucumber 10 may also be a very good source of B vitamins, which can provide energy and reduce the fatigue felt during an alcoholic hangover. Cucumber 10 may also help to reduce headaches caused by hangovers because of the sugars, B vitamins, and electrolytes found in cucumber 10. The boost of energy received by cucumber 10 helps to reduce fatigue and muscular weakness experienced during an alcoholic hangover. Cucumber 10 may also aid in healthy digestion as it is a remedy for individuals with chronic constipation. Because cucumber 10 helps with digestion it helps promote bowel movement. Bowel movement leads to defecation, which helps to cleanse the body of toxins by flushing them out of the digestive system. This flush of the digestive system helps to promote hunger and normal food consumption. Once the body's intestines have been emptied of non-nutrition bearing waste, there is available space in the body's intestines for healthy fresh foods to be ingested.

Without being bound by theory, romaine lettuce 14 may be a very good source of vitamin K, which can prevent cirrhosis of the liver by preventing vitamin K deficiency-induced bleeding in the intestines and liver. Vitamin K deficiency can be caused by drinking alcohol in excess amounts and can lead to vitamin K deficiency-induced bleeding in the intestines and liver while an individual is hung-over. There is 100 percent or more RDA (recommended daily allowance) of vitamin K in an effective amount of the present composition. In a 10 ounce drink comprising the most preferred percentage amounts of red onion juice, cucumber juice, and a leafy green vegetable juice there is approximately 250 percent RDA of Vitamin K. Romaine lettuce 14 may also be a significant source of folate. Alcohol interferes with the absorption of folate, so persons who drink excessively are at risk for folate deficiency anemia. Signs of folate deficiency anemia include decreased appetite, irritability, lack of energy, and diarrhea. There is 30 percent or more RDA of folate in an effective amount of the present composition. In a 10 ounce drink comprising the most preferred percentage amounts of red onion juice, cucumber juice, and a leafy green vegetable juice there is approximately 75 percent RDA of folate. Romaine lettuce 14 is also alkaline forming. Alcohol consumption causes the acid/alkaline balance of the body to become abnormal. The alkaline forming minerals in romaine lettuce 14 may help remove toxins and keep one's acid/alkaline balance in order. Romaine lettuce 14 may also be a very good source of vitamin A and beta-carotene. Alcohol consumption results in a significant depletion of hepatic vitamin A. There is 150 percent or more RDA of vitamin A in an effective amount of the present composition. In a 10 ounce drink comprising of the most preferable percentage amounts of red onion juice, cucumber juice, and a leafy green vegetable juice there is approximately 375 percent RDA of Vitamin A. Depletion of hepatic vitamin A can lead to fatty liver, alcoholic hepatitis, and cirrhosis of the liver. Beta-carotene is a precursor to vitamin A and allows for vitamin A absorption. Since romaine lettuce 14 contains high levels of vitamin A and beta-carotene, consumption of romaine lettuce 14 is effective for treating this deficiency. Beta-carotene in food is safe for alcohol drinkers, but it can be toxic for alcohol drinkers when it is taken as a pill supplement. In alcohol drinkers, there is a toxic reaction that occurs between beta-carotene supplements and ethanol. Thus, food and juice consumption appears to be the effective way to safely recover from a vitamin A deficiency. Early symptoms of liver disease include fatigue and loss of energy, poor appetite and weight loss, and nausea or belly pain. These symptoms are effectively treated with romaine lettuce 14.

Romaine lettuce 14, however, can be substituted for one or more raw leafy greens including butterhead lettuce 15, oakleaf lettuce 16, turnip greens 17, or spinach 18. If spinach is undersirable, then any spinach-free leafy greens or spinach-less leafy greens can be used. All of these leafy greens contain similar levels of vitamin A, beta-carotene, vitamin K, and folate.

Figure 5:
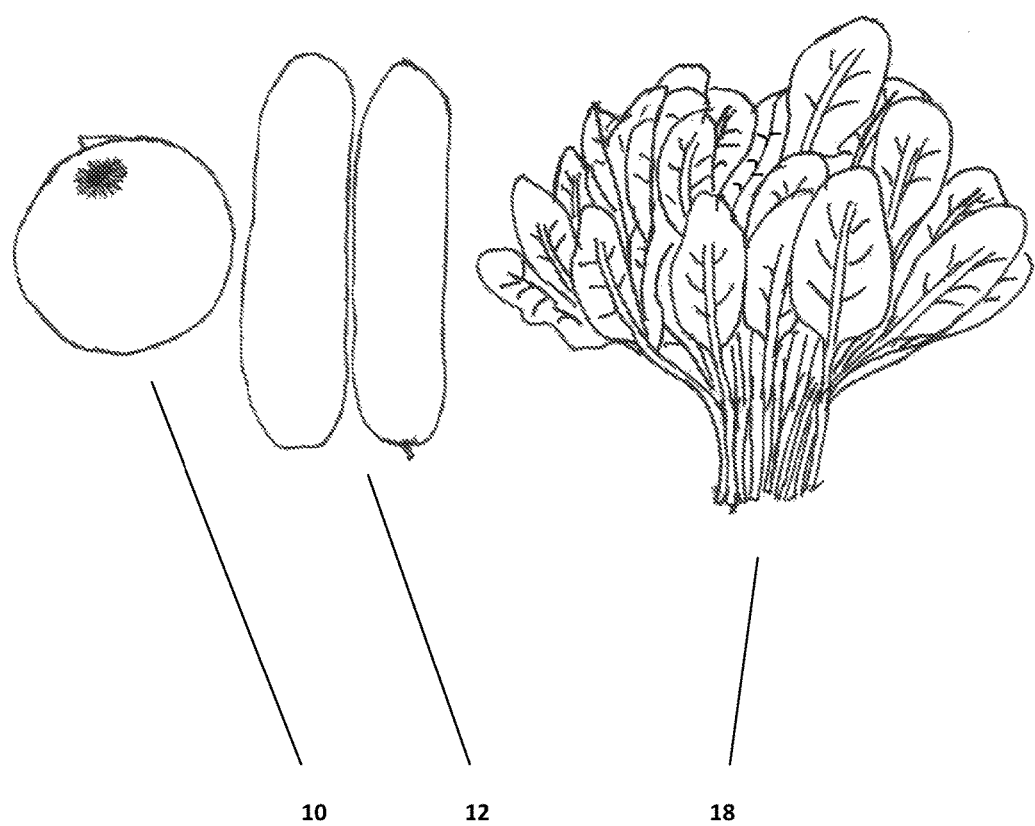
FIG. 5 shows raw elements for a fifth embodiment of a composition for a hangover treatment.

Juice drink 40 in FIG. 5 is one embodiment of the final version of the composition for hangover treatment sold to consumers. The manner of using the product will be the same for all juice embodiments. Typically, the hangover treatment is used after the drinker drinks alcohol, falls asleep, then wakes up with a hangover. Typically, this occurs the morning after drinking when the hangover symptoms are present. However, some may drink alcohol during the day, fall asleep, and wake up in the evening or at night with a hangover. Preferably, the product should first be completely consumed within a short period of time (e.g., within about five minutes). After drinking the product, it is preferable that one does not lie down horizontally for approximately 30 minutes in order to allow the juice to run through one's system. It will coat one's stomach and stomach pain should immediately begin to subside. During this approximate 30-minute period, one should not drink or consume anything else except for water. If the mixture is thrown up (i.e. vomiting occurs), a second dose of the juice should be consumed. If one feels like throwing up or is sick to the stomach for more than thirty minutes after taking the composition for treating a hangover, it may be best to throw up and take another dose. There may be a backup of bile from the liver inside one's stomach (due to excessive drinking) and this bile needs to be cleaned out before one can properly digest the composition. This is a common problem called bile reflux where there is a backflow of bile into the stomach that connects to the liver and gallbladder.

Figure 10:
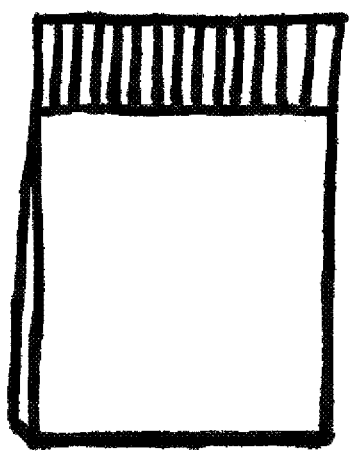
FIG. 10 is an embodiment of the final powdered juice product containing a composition of the hangover treatment.

Juiced powder 42 in FIG. 10 is a second embodiment of the composition for hangover treatment sold to consumers. The manner of using the product will be the same for all powdered embodiments. The juiced powder 42 may be reconstituted in a liquid to create a reconstituted composition before being consumed. Mixing of the juiced powder with a liquid, such as soup will help to improve flavor for consumption. The liquid may be vegetable broth, chicken broth, beef broth, vegetable soup, chicken soup, liquid chicken stock, liquid beef stock, liquid vegetable stock, water, milk, vegetable juice, fruit juice, and the like. The liquid should not be tomato based because a tomato based liquid may be too acidic and could aggravate hangover symptoms while at the same time countering the effects of the hangover treatment. Preferably the liquid is a broth. Most preferably the liquid is chicken broth. The use of chicken broth adds to the efficacy of the hangover drink because of the anti-nausea effect of chicken broth which will help prevent throwing up of the composition. The reconstituted composition can be consumed immediately or heated for consumption. The method used for heating the reconstituted composition may be by microwave, stove, oven, grill, or any other heating method or device meant for warming up food or drinks. Preferably, the reconstituted composition is heated up in the microwave in a bowl or in a pot on a gas or electric range.

Preferably, the hangover treatment is used after the drinker has fallen asleep after drinking and has woken up and the hangover symptoms are present. Typically, this is in the morning; however, some may drink during the day, fall asleep, and wake up in the evening or at night with a hangover. Preferably, the product should first be completely consumed within a short period of time (within about five minutes). After drinking the product or eating it in a soup, it is preferable that one does not lie down horizontally for approximately 30 minutes in order to allow the powdered juice mixture to run through one's system. It will coat one's stomach and stomach pain will immediately begin to subside. During this approximate 30-minute period, one should not drink or consume anything except for water. If the mixture is thrown up (i.e. vomiting occurs), a second dose of powdered juice mixture will have to be consumed. If one feels like throwing up or is sick to the stomach for more than thirty minutes after taking the hangover drink, it may be best to throw up and take another dose. There may be a backup of bile from the liver inside one's stomach (due to excessive drinking) and this bile needs to be cleaned out before one can properly digest the hangover drink. This is a common problem called bile reflux where there is a backflow of bile into the stomach from the bile tract that connects to the liver and gallbladder.

The composition for hangover treatment will alleviate hangover symptoms by cleansing out the body and filtering out the toxins, while replacing nutrients. If the amount of nutrients lost is significant, then the effective amount of the composition an individual will need to consume will be more than if the individual had lost fewer nutrients from drinking alcohol.

If the individual has been drinking for multiple days, this will also affect the amount of nutrients lost from the body and will increase the effective amount of the hangover treatment that is necessary to treat the individual's hangover symptoms. Hangover symptoms will be more severe and a larger dose of the hangover treatment will need to be consumed.

Alcohol is a diuretic, meaning that it increases urination. This increased urination decreases the normal levels of potassium in the body as potassium is lost during urination. To regain normal levels, it is advised to consume non-acidic foods high in potassium throughout the day such as cantaloupe, banana, watermelon, honey dew melon, potatoes, beans, milk, yogurt, cottage cheese, chicken, turkey, salmon, cod, flounder, beef, wheat bread, whole grains, brown rice, and bran. The foods mentioned above should be consumed intermittently throughout the day even after symptoms have subsided. The body increases levels of potassium in the body very slowly and it may take up to 24 hours for the body to obtain sufficient and stable potassium levels.

One should avoid eating any foods or food products containing high-acid fruits or vegetables such as tomatoes, grapefruits, limes, lemons, kiwis, olives, or pickles. These acidic fruits and vegetables will upset the stomach and reverse the beneficial effect of the hangover treatment. One should also not eat greasy foods, such as anything fried or deep fried, within 24 hours of using the hangover treatment. The oil in greasy foods sticks to the stomach lining and makes it more difficult for the body to absorb nutrients, which the body needs during a hangover. Greasy foods would also increase the body's blood pressure, which would counter the health effects of the hangover treatment. One should also avoid eating any tomato-based foods or drinks at any time while using the hangover treatment and up to 24 hours after consumption. Tomatoes are very difficult for the body to process and are very acidic. Tomato-based products will add stress to the body, increase the symptoms of the hangover, and counter the effects of the hangover treatment.

The standard time it takes to alleviate the symptoms of a hangover is about four hours from the time of consumption of the composition for treating hangovers. If a hangover persists, one should use another dose of the composition for treating hangover. The composition for treating hangover acts like a cleanse for one's body and so the process is a gradual improvement over time. It is not like headache medicine which reduces symptoms for a certain period of time. The hangover treatment effectively eradicates the hangover. Since the hangover treatment brings on a gradual improvement to one's body, it is recommended to go outdoors for fresh air and sun light. Fresh air and sunlight help to sooth one's body while the hangover treatment takes effect.

An advantage of the composition for hangover drink is that the effective amount of the ingredients is normally too much to be eaten when not in juice or powdered juice form. The actual mass of the ingredients that must be consumed is more than most individuals can consume in a single sitting because it is too much food to be consumed into one's stomach. When an individual drinks the juice or powdered juice mixture it is a reduction of mass of the raw ingredients without a reduction of the amount of nutrients obtained from the raw, unprocessed ingredients. The fibers and non-juice able matter is removed and the juice product is thus significantly reduced in volume as compared to the volume of the raw, unprocessed ingredients.

The juice and powdered juice composition of the hangover treatment allows one's body to process the nutrients more quickly and effectively than in its raw, unprocessed form because the nutrients can be obtained without breaking down the fibers and pulp of the ingredients. This means that the hangover symptoms will be treated more quickly and effectively.

The juice and powdered juice compositions are also much more easily consumed because they do not require chewing. When an individual is hungover, the individual is fatigued and will have a hard time chewing. In order to consume an effective amount of the hangover treatment in its raw form the individual may have to chew for 20 minutes and up to an hour. This is very difficult for an individual that is hungover. The juice composition can be consumed within less than a minute if gulped down and within seconds if a straw is used to drink the composition.

The juice and powdered juice compositions are also less potent in smell and will leave behind less of a smell in an individual's mouth than if the ingredients are consumed in raw, unprocessed form because of the amount of time of contact to the gum and teeth area. When the juice is consumed, it is swallowed quickly and leaves behind minimal onion smell. If an individual were to eat the raw, unprocessed ingredients, he or she would have to thoroughly chew the ingredients for up to an hour and this smell would linger in the mouth even after flossing, brushing with toothpaste, and rinsing with mouthwash.

The juice and powdered juice compositions are also more easily consumed than a blended product of the raw ingredients because the pulp of the ingredients is very thick and cannot be consumed by an individual without extreme difficulty. The consistency of the raw ingredients when blended is that of a thick clumpy salsa. The composition of raw ingredients when blended is very harsh in flavor and the effective amount necessary to alleviate a hangover is too massive for an individual to consume in one sitting.

The composition of the hangover treatment comprises ingredients that are widely produced and readily available year round in the United States. The juice and powdered juice can be produced at any time during the year because red onion, cucumber, and leafy green vegetables are not seasonal and are harvested and sold year round.

The powdered juice, after vacuum sealing in a package, has a longer shelf life than the raw ingredients alone. The shelf life of the packaged powdered juice is two to three years while the shelf life of the raw ingredients is one to ten days.

The powdered juice takes up less shelf space than the raw ingredients because an effective amount of the powdered juice is only one-quarter ounce to 4 ounces while an effective amount of the raw ingredients is 9.5 ounces to 24 ounces.

The powdered juice reduces the shipping and storage costs because the weight of an effective amount of the powdered juice is only one-quarter ounce to 4 ounces while the weight of an effective amount of the raw ingredients is 9.5 ounces to 24 ounces. The powdered juice also takes up less area than the raw ingredients so a greater number of powdered juice containers can be shipped and stored in the same space. The amount of single servings that can be shipped and stored in the powdered juice form is six to nineteen times more servings than would be in raw form.

The powdered juice does not require refrigeration like the raw ingredients because the juiced raw ingredients have been spray dried to a powder and vacuum sealed. This reduces the cost to ship and store and allows for the product to be displayed in any location of any store without the use of limited refrigerator shelf space.

The powdered juice is also cheaply packaged. A single sized foil container for packing costs one to two cents per bag.

Applicant's invention is useable in any environment, making it portable and widely saleable. It comprises ingredients that are not seasonal and are sold year round. It can be produced in many regions of the world because of the wide availability of red onion, cucumber, and other leafy greens. It helps to reduce the effects of withdrawals from alcohol poisoning making it a likely treatment of alcoholism. It is easier to consume as a drink and powdered drink then in its raw elements. It more effectively coats the stomach as a drink and powdered soup than it does when consumed in its raw elements, reducing the acidity and soothing the stomach more quickly. It is consumed as a liquid drink or powdered drink mix, which minimizes both the strength of the products odor in the mouth and length of time the products odor is present in the mouth. If the raw ingredients are consumed by chewing, an unpleasant odor lingers in the mouth that is hard to remove and can last for many hours. It can be consumed without cutting red onion, which can irritate the eyes. It is rapidly processed by the body in juice form as the body does not have to break down the pulp of the product to process the nutrients.

Figure 2:
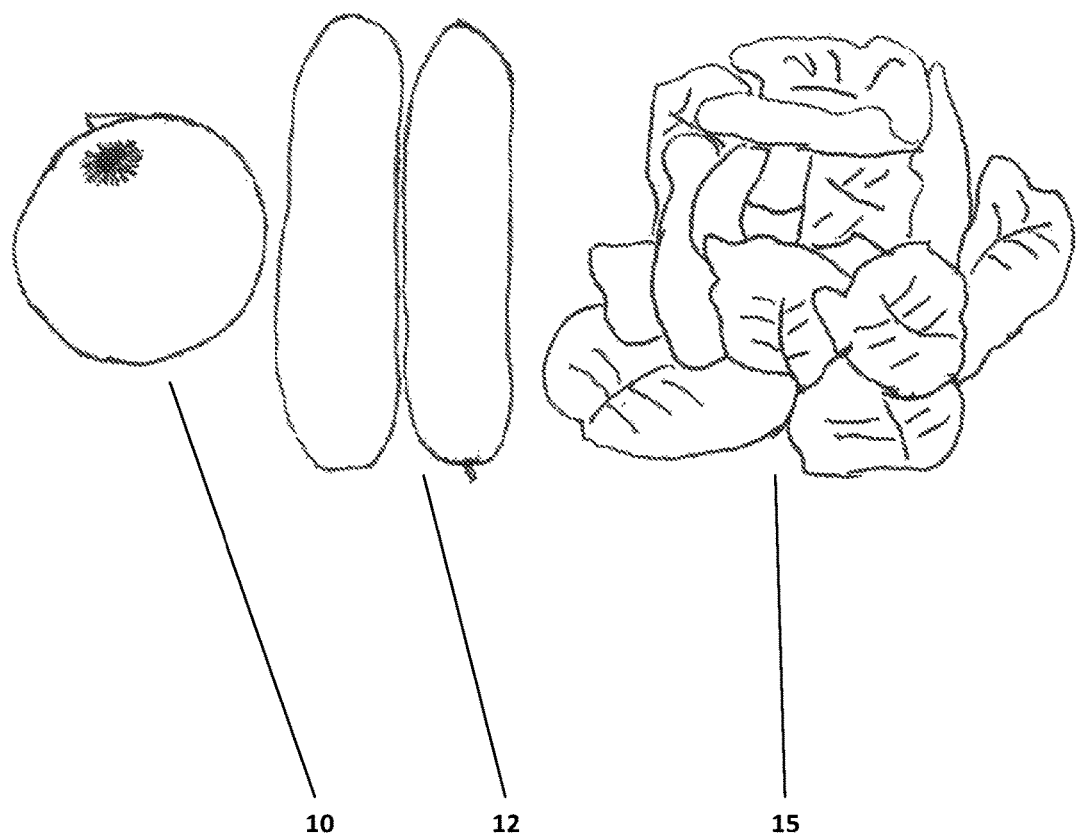
FIG. 2 shows raw elements for a second embodiment of the composition for a hangover treatment.
Figure 3:
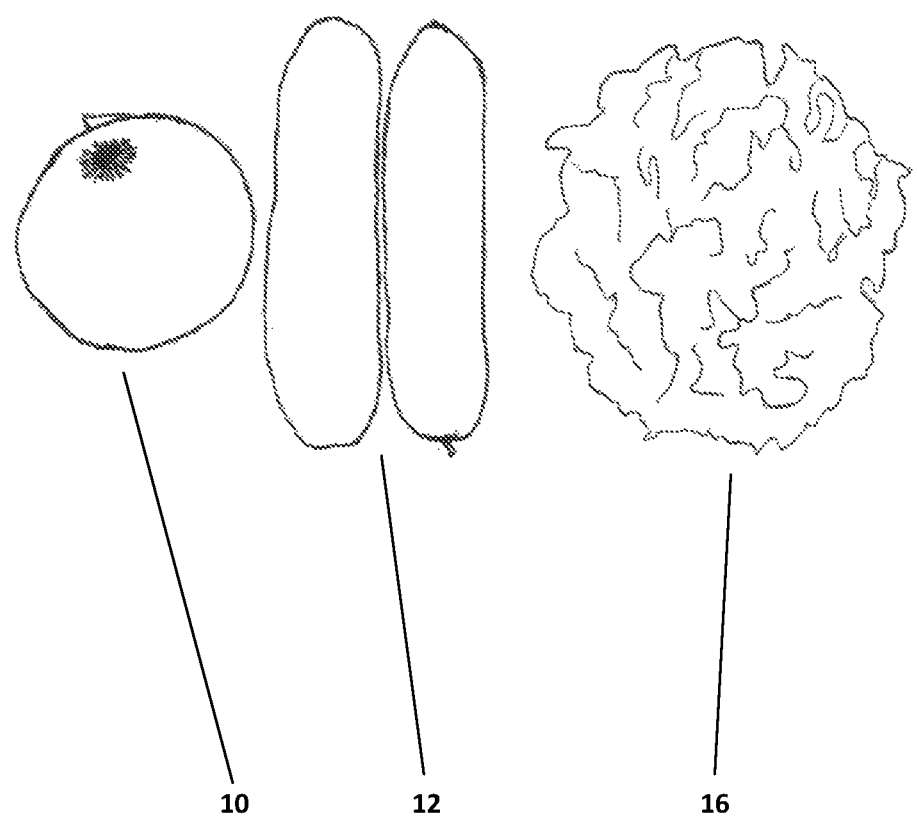
FIG. 3 shows raw elements for a third embodiment of a composition for a hangover treatment.
Figure 4:
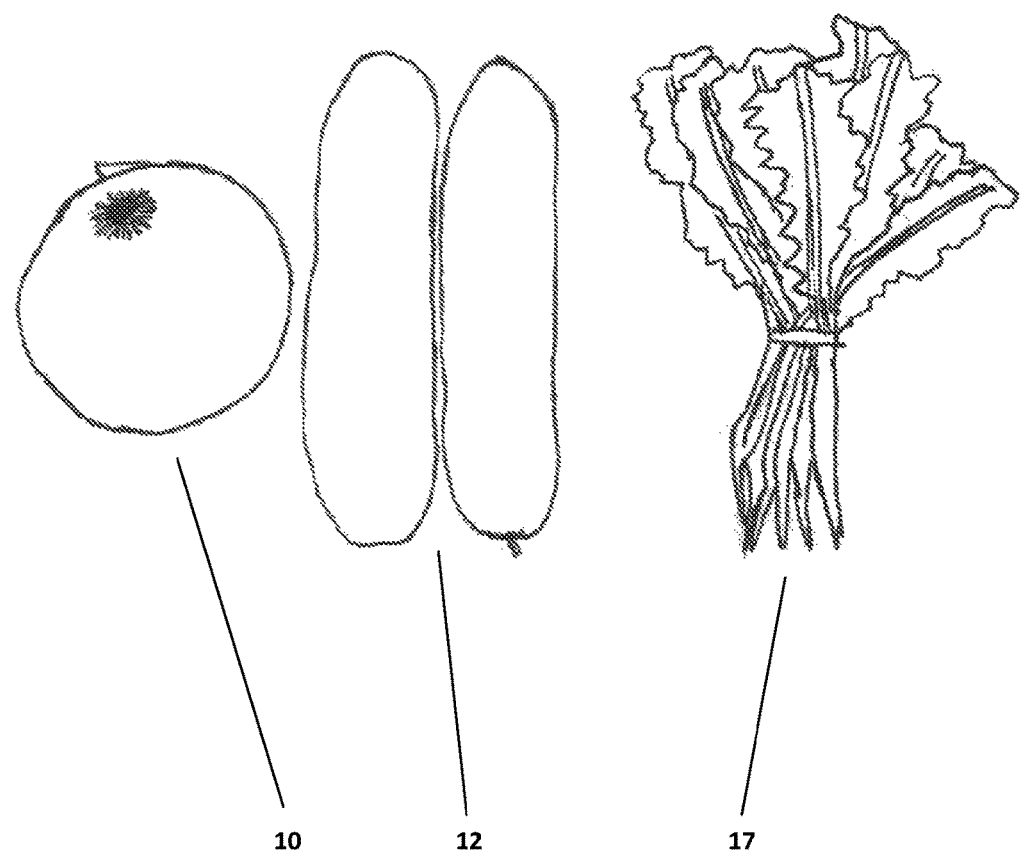
FIG. 4 shows raw elements for a fourth embodiment of a composition for a hangover treatment.

There are various possibilities with regard to the leafy green vegetables of the composition for hangover treatment. For example, romaine lettuce 14 as shown in FIG. 1 can be substituted with one or more raw leafy greens or spinach-free leafy greens, including butterhead lettuce 15, oakleaf lettuce 16, turnip greens 17, or spinach 18. All of these leafy greens contain similar high amounts of vitamin A, beta-carotene, vitamin K, and folate. FIG. 2 is another embodiment containing butterhead lettuce 15 as the leafy green. FIG. 3 is another embodiment containing oakleaf lettuce 16 as the leafy green. FIG. 4 is another embodiment containing turnip greens 17 as the leafy green. FIG. 5 is another embodiment containing spinach 18 as the leafy green. In some embodiments, the leafy green vegetable component can be a combination of any of the leafy green vegetables.

Although the leafy green vegetable may be different for each embodiment, the first two elements, red onion 10 and cucumber 12, remain the same. Some embodiments may also include flavorings, which may or may not have any health benefits. Flavorings may be added and may change with market preferences and after ongoing market research. Flavorings for future embodiments may include pineapple juice.

Example #1

Dates of Experiment
Aug. 15, 2013, Aug. 18, 2013, Aug. 20, 2013, Aug. 31, 2013, Sep. 3, 2013, Sep. 7, 2013, Sep. 8, 2013, Sep. 12, 2013

Purpose

This study was performed to test "the Composition and Method for Treating a Hangover" in order to test its effectiveness. This study was performed on ten participants of various age and sex. The study was done the following day after consumption of alcohol. The participants were no longer intoxicated at the time of the study and were experiencing hangovers of different severity and intensity. Each participant consumed one 10 ounce drink comprising, by weight of the juice, 10-25 percent red onion juice, 20-60 percent romaine lettuce juice, and 30-70 percent cucumber juice.

Materials

A single 10 ounce drink per participant which contains the first embodiment of the composition (Red Onion Juice, Cucumber Juice, and Romaine Lettuce Juice)

A Hangover study questionnaire

Procedure

Direct each participant to fill out the first page of the study and answer questions 1-6 of the study.

Question #1: How many days a week do you drink 4 or more alcoholic beverages?

Question #2: On the nights you drink 4 or more alcoholic beverages, how many drinks do you normally consume in an average night?

Question #3: What types of alcoholic drinks do you normally consume in a night (beer, liquor, wine)?

Question #4: On nights when you drink 4 or more alcoholic beverages, how many of those nights typically result in a hangover the next day?

Question #5: How did you feel before taking the Hangover Drink? What are your ailments (i.e. weak stomach, vomiting, upset stomach, acidic stomach, nausea, dehydration, elevated body temperature, high blood pressure, rapid heart rate, heart palpitations, difficulty concentrating, bloodshot eyes, trouble sleeping, depression, anxiety, irritability, sensitivity to light and noise, blurred vision, dizziness, cold sweats, muscular weakness, fatigue, muscle aches, general pain, labored breathing, erratic motor functions, headache etc. . . . )?

Question #6: On a scale of 1 to 10, with 1 being the least hung-over and 10 being the most hung-over, how hung-over would you say you felt before taking the hangover drink?

Give each participant the ten ounce drink and direct them to drink it. Make sure it is completely consumed within 5 minutes.

Five minutes after consumption, direct each participant to fill out question 7.

Question #7: How did you feel within the first 5 minutes of taking the Hangover Drink?

One hour after consumption, direct each participant fill out question 8.

Question #8: How did you feel one hour after taking the Hangover Drink? Have any of your ailments been reduced? By how much?

Two hours after consumption, direct each participant to fill out question 9.

Question #9: How did you feel 2 hours after taking the Hangover Drink? Have any of your ailments been reduced? By how much?

Four hours after consumption, direct each participant to fill out questions 10-12 and sign the questionnaire.

Question #10: How did you feel 4 hours after taking the Hangover Drink?

Question #11: Do you believe that the Hangover Drink had an effect on the severity and length of your hangover? If so, please explain how you felt and what difference the hangover drink made.

Question #12: If you had the opportunity to use this product in the future, how likely would you decide to use it on a scale of 1 to 10 with one being least likely to use it and 10 being the most likely to use it?

If any additional results were noticed after the allotted 4 hours of the study, the participant should add those comments along with the number of hours these results were noticed after consumption.

Results

In example #1, 10 participants had been drinking alcohol in the prior night and were no longer intoxicated the following morning, but were experiencing hangovers of different severities on scale of 1 to 10, with 1 being the least hungover and 10 being the most. Results of the study are shown in FIG. 8. The average number of drinks consumed in the prior night by the participants was 9 drinks of beer and/or liquor and/or wine and/or champagne and/or mixed alcoholic beverages. The average age of the participants was 29 years of age. The average hangover severity was level 6 before taking the composition for treating hangover. The morning after the drinking episode, the subjects were given 10 ounces of the composition for treating hangover.

After the participants were given the 10-ounce serving of the composition for treating hangover and were examined to determine what hangover symptoms were alleviated, how long it took for the composition to have a beneficial effect, and how long until the composition alleviated the hangover completely. Fifty percent of participants felt an improvement in their symptoms within the first 5 minutes after consumption. Eighty percent of participants felt an improvement within the first hour after consumption and 100 percent of participants felt an improvement in their symptoms within the first 2 hours after consumption. While, the average time a hangover will last for most individuals can range from 8 hours to 48 hours, 10 percent of participants were relieved of their hangover around 1 hour after consumption, 70 percent of participants were relieved of their hangover around 4 hours after consumption, and 10 percent of participants were relieved of their hangover around 6 hours after consumption. The 1 other participant (10 percent of the participants) who did not have complete hangover relief had a hangover reduction from a maximum level of 10 to a hangover of level 3 out of 10. One hundred percent of participants stated that the drink made a difference in the severity and length of their hangover.

One participant said that she remained hung-over only because she "did not have any more" of the hangover drink to consume. If this participant had been given a larger serving of the hangover drink to begin with or was given a second subsequent serving, her hangover may have subsided like the rest of the participants within the 4 hour standard period. This study proves that the applicant's invention is effective for the purpose of relieving hangover symptoms.

Prophetic Example #1

Purpose

This study will be performed to test "the Composition and Method for Treating a Hangover" in order to test and compare the effectiveness of the composition for treating hangover comprising by weight, approximately 10 percent to approximately 25 percent red onion, approximately 20 percent to approximately 60 percent romaine lettuce, and approximately 30 to approximately 70 percent cucumber with a drink consisting essentially of, by weight of the composition, 100 percent romaine lettuce juice, a drink consisting essentially of, by weight of the composition, 100 percent cucumber juice, a drink consisting essentially of, by weight of the composition, 100 percent red onion juice, and a composition for treating hangover comprising by weight, approximately 10 percent to approximately 25 percent red onion, approximately 20 percent to approximately 60 percent romaine lettuce, and approximately 30 to approximately 70 percent cucumber, and, approximately 3 percent to approximately 25 percent juiced pineapple. This study will be performed on participants of various age and sex. The study will be done the following day after consumption of alcohol. The participants will no longer be intoxicated at the time of the study and will be experiencing hangovers of different severity and intensity. Each participant will consume one 10 ounce drink. Each drink will be labeled with a number between 1 and 5 containing one of the drinks described above. The participants will not know which drink of the five they are consuming and will be asked to be as objective as possible when making their analysis of the drink during the questions portion of the study. It is hypothesized that for those participants that consume the composition for treating hangovers, their hangover symptoms will be significantly reduced or completely eliminated within a span of four hours from the time of consumption of the composition. It is also hypothesized that those who consume the control drinks will see some improvement, but will not have a substantial reduction or complete reduction of their hangover symptoms and that their hangovers will continue after the 4 hour period allotted for the hangover drink study.

Materials to be Used

A single 10 ounce drink per participant which contains by weight of the juice, either 100 percent romaine lettuce juice, or 100 percent cucumber juice, or 100 percent red onion juice, or the first embodiment of the composition for treating hangovers (10-25 percent red onion juice, 20-60 percent romaine lettuce juice, and 30-70 percent cucumber juice), or the second embodiment of the composition for treating hangovers (10-25 percent red onion juice, 20-60 percent romaine lettuce juice, 30-70 percent cucumber juice, and 3-25 percent pineapple juice).

A hangover study questionnaire

Procedure to be Followed

Direct each participant to fill out the first page of the study and answer questions 1-6 of the study.

Question #1: How many days a week do you drink 4 or more alcoholic beverages?

Question #2: On the nights you drink 4 or more alcoholic beverages, how many drinks do you normally consume in an average night?

Question #3: What types of alcoholic drinks do you normally consume in a night (beer, liquor, wine)?

Question #4: On nights when you drink 4 or more alcoholic beverages, how many of those nights typically result in a hangover the next day?

Question #5: How did you feel before taking the Hangover Drink? What are your ailments (i.e. weak stomach, vomiting, upset stomach, acidic stomach, nausea, dehydration, elevated body temperature, high blood pressure, rapid heart rate, heart palpitations, difficulty concentrating, bloodshot eyes, trouble sleeping, depression, anxiety, irritability, sensitivity to light and noise, blurred vision, dizziness, cold sweats, muscular weakness, fatigue, muscle aches, general pain, labored breathing, erratic motor functions, headache, inability to eat solid foods, lack of hunger etc. . . . )?

Question #6: On a scale of 1 to 10, with 1 being the least hung-over and 10 being the most hung-over, how hung-over would you say you felt before taking the hangover drink?

Give each participant the ten ounce drink and direct them to drink it. Make sure it is completely consumed within 5 minutes.

Five minutes after consumption, direct each participant to fill out question 7.

Question #7: How did you feel within the first 5 minutes of taking the Hangover Drink? Do you feel a reduction in your hangover? If so how would you rate your hangover on a scale from 1-10?

One hour after consumption, direct each participant fill out question 8.

Question #8: How did you feel one hour after taking the Hangover Drink? Have any of your ailments been reduced? How would you rate your hangover on a scale from 1-10?

Two hours after consumption, direct each participant to fill out question 9.

Question #9: How did you feel 2 hours after taking the Hangover Drink? Have any of your ailments been reduced? How would you rate your hangover on a scale from 1-10?

Four hours after consumption, direct each participant to fill out questions 10-12 and sign the questionnaire.

Question #10: How did you feel 4 hours after taking the Hangover Drink? Have any of your ailments been reduced? How would you rate your hangover on a scale from 1-10?

Question #11: Did the hangover drink have a positive effect on your general health and well being? Did the hangover drink make a significant impact on your hangover and all its symptoms as a whole? If so, please explain how you felt and what difference the hangover drink made.

Question #12: If you had the opportunity to use this product in the future, how likely would you decide to use it on a scale of 1 to 10 with one being least likely to use it and 10 being the most likely to use it?

If any additional results were noticed after the allotted 4 hours of the study, the participant should add those comments in question #13 along with the number of hours these results were noticed after consumption of the drink.

Speculative Results

It is believed that the participants of the study that will consume a drink consisting essentially of, by weight of the juice, 100 percent juiced cucumber, 100 percent juiced romaine lettuce, or 100 percent juiced red onion juice, will not be cured of their hangover symptoms completely.

With respect to the red onion juice, some participants will not be able to drink the juiced red onion drink without throwing up. The participants that will throw up, will feel better after throwing up, but will not be cured of their hangover symptoms.

The participants of the study that will consume a drink comprising, by weight of the juice, 10-25 percent juiced red onion, 20-60 percent juiced romaine lettuce, and 30-70 percent juiced cucumber, will feel a major reduction in most or all of their hangover symptoms or will be completely cured of their hangover within a span of 4 hours from the time of consumption of the juiced drink.

The participants of the study that will consume a drink comprising, by weight of the juice, 10-25 percent juiced red onion, 20-60 percent juiced romaine lettuce, 30-70 percent juiced cucumber, and 3-25 percent juiced pineapple will feel a major reduction in most or all of their hangover symptoms or will be completely cured of their hangover within a span of 4 hours from the time of consumption of the juiced drink.

This study will demonstrate that the composition for treating hangovers, with our without flavoring are effective for the purpose of relieving hangover symptoms. This study will also demonstrate that the components of the invention create a novel synergistic effect because the combination creates a greater effect than the effects of the components separately.

Prophetic Example #2

Purpose

This study will be performed to test "the Composition and Method for Treating a Hangover" in order to test the effectiveness of a dehydrated vegetable powder additive for a soup comprising the composition for treating hangovers. This study will be performed on participants of various age and sex. The study will be done the following day after consumption of alcohol. The participants will no longer be intoxicated at the time of the study and will be experiencing hangovers of different severity and intensity. Each participant will consume a one ounce portion of the vegetable powder. The powder will be mixed with 14 ounces of chicken broth and heated up for consumption. Participants will be given a soup mixed with a one ounce powder comprising, by weight of the powder, approximately 10 percent to approximately 25 percent red onion juiced powder, approximately 20 percent to approximately 60 percent romaine lettuce juiced powder, and approximately 30 percent to approximately 70 percent cucumber juiced powder. It is hypothesized, that their hangover symptoms will be majorly reduced or completely eliminated within a span of four hours from the time of consumption of the composition.

Materials to be Used

A single one ounce powdered drink which contains by weight of the juice, the second embodiment of the hangover treatment approximately 10 percent to approximately 25 percent red onion juiced powder, approximately 20 percent to approximately 60 percent romaine lettuce juiced powder, and approximately 30 percent to approximately 70 percent cucumber juiced powder.

A 14 ounce chicken broth soup

A hangover study questionnaire

Procedure to be Followed

Before the participants drink the heated powdered soup mixture (heated powdered soup and chicken broth mixture), direct each participant to fill out the first page of the study and answer questions 1-6 of the study.

Question #1: How many days a week do you drink 4 or more alcoholic beverages?

Question #2: On the nights you drink 4 or more alcoholic beverages, how many drinks do you normally consume in an average night?

Question #3: What types of alcoholic drinks do you normally consume in a night (beer, liquor, wine)?

Question #4: On nights when you drink 4 or more alcoholic beverages, how many of those nights typically result in a hangover the next day?

Question #5: How did you feel before eating the Hangover soup mixture? What are your ailments (i.e. weak stomach, vomiting, upset stomach, acidic stomach, nausea, dehydration, elevated body temperature, high blood pressure, rapid heart rate, heart palpitations, difficulty concentrating, bloodshot eyes, trouble sleeping, depression, anxiety, irritability, sensitivity to light and noise, blurred vision, dizziness, cold sweats, muscular weakness, fatigue, muscle aches, general pain, labored breathing, erratic motor functions, headache, inability to eat solid foods, lack of hunger etc. . . . )?

Question #6: On a scale of 1 to 10, with 1 being the least hung-over and 10 being the most hung-over, how hung-over would you say you felt before consuming the heated hangover soup mixture?

Give each participant a bowl containing a heated 14 ounce chicken broth mixed with the one ounce powdered drink. Make sure it is completely consumed within five to ten minutes. Five minutes after consumption, direct each participant to fill out question 7 and 8.

Question #7: How did the hangover mixture taste? On a scale of 1 to 10, with one being unpalatable and ten being delicious, how would you rate the flavor of the mixture. What sort of spice or flavor do you think would help increase flavor and palatability?

Question #8: How did you feel within the first 5 minutes of taking the hangover soup mixture? Do you feel a reduction in your hangover? If so how would you rate your hangover on a scale from 1-10?

One hour after consumption, direct each participant fill out question 9.

Question #9: How did you feel one hour after taking the hangover soup mixture? Have any of your ailments been reduced? How would you rate your hangover on a scale from 1-10?

Two hours after consumption, direct each participant to fill out question 10.

Question #10: How did you feel 2 hours after taking the hangover soup mixture? Have any of your ailments been reduced? How would you rate your hangover on a scale from 1-10?

Four hours after consumption, direct each participant to fill out questions 11-13 and sign the questionnaire.

Question #11: How did you feel 4 hours after consuming the hangover soup mixture? Have any of your ailments been reduced? How would you rate your hangover on a scale from 1-10?

Question #12: Did the hangover soup mixture have a positive effect on your general health and well being? Did the hangover soup mixture make a significant impact on your hangover and all its symptoms as a whole? If so, please explain how you felt and what difference the hangover soup mixture made.

Question #13: If you had the opportunity to use this product in the future, how likely would you decide to use it on a scale of 1 to 10 with one being least likely to use it and ten being the most likely to use it?

If any additional results were noticed after the allotted 4 hours of the study, the participant should add those comments in question #14 along with the number of hours these results were noticed after consumption of the heated powdered soup mixture.

Speculative Results

The participants of the study that consume a powdered soup mixture comprising, chicken broth and a vegetable juiced powder by weight of the powder, approximately 10 percent to approximately 25 percent red onion juiced powder, approximately 20 percent to approximately 60 percent romaine lettuce juiced powder, and approximately 30 percent to approximately 70 percent cucumber juiced powder, will feel a major reduction in most or all of their hangover symptoms or will be completely cured of their hangover within a span of 4 hours from the time of consumption of the powdered juice and chicken broth mixture. The participants will like the flavor of the soup and it will score an average flavor of 6 to 9. The nausea of the participants will be reduced.

This study will demonstrate that the powdered form of the invention is effective for the purpose of relieving hangover symptoms. The study will also demonstrate that the present invention in powdered form when mixed with chicken broth and heated is palatable and flavorful to a majority of participants. This study will also demonstrate that the components of the present invention create a novel synergistic effect because the combination creates a greater effect than the sum of the effects of the components separately.

While the above description contains much specificity, it should not be construed as limitations on the scope, but rather as an exemplification of several embodiments thereof. Many other variations are possible. Accordingly, the scope should be determined not by the embodiments illustrated, but by the appended claims and their legal equivalents.

What is claimed is:

1. A method for treating a hangover, comprising administering to a subject in need thereof a composition, comprising:
   a. juiced onions present in an amount of approximately 5 percent to approximately 30 percent of a total weight of the composition;
   b. juiced cucumbers present in an amount of approximately 15 percent to approximately 80 percent of the total weight of the composition; and
   c. juiced leafy green vegetables present in an amount of approximately 15 percent to approximately 80 percent of the total weight of the composition, whereby the hangover is alleviated.

2. The method of claim 1, wherein the composition is administered every 4 hours as needed.

3. The method of claim 1, wherein the composition is administered when the subject is no longer intoxicated, but while the subject still has the hangover.

4. The method of claim 1, wherein the onion is red onion.

5. The method of claim 4, wherein the leafy green vegetable is selected from the group consisting of romaine lettuce, butterhead lettuce, oakleaf lettuce, turnip greens, and spinach.

6. The method of claim 5, wherein the red onion is present in an amount of approximately 10 percent to approximately 25 percent of the total weight of the composition.

7. The method of claim 6, wherein the leafy green vegetable is present in an amount of approximately 20 percent to approximately 60 percent of the total weight of the composition.

8. The method of claim 6, wherein the cucumber is present in an amount of approximately 30 percent to approximately 70 percent of the total weight of the composition.

9. The method of claim 1, wherein the juiced onions, the juiced cucumbers, and the juiced leafy green vegetables are in powder form and reconstituted in a liquid for consumption.

10. The method of claim 9, wherein the liquid is a soup broth.

11. The method of claim 10, wherein the soup broth is chicken soup.

12. A method for treating a hangover in a subject in need thereof, comprising:
   a. reconstituting a powdered composition in a liquid to form a reconstituted composition, the powdered composition comprising onion juiced powder present in an amount of approximately 5 percent to approximately 30 percent of a total weight of the powdered composition, cucumber juiced powder present in an amount of approximately 15 percent to approximately 80 percent of the total weight of the powdered composition; and leafy green vegetable juiced powder present in an amount of approximately 15 percent to approximately 80 percent of the total weight of the powdered composition; and
   b. administering the reconstituted composition to the subject, whereby the hangover is alleviated.

13. The method of claim 12, wherein the reconstituted composition is administered every 4 hours as needed.

14. The method of claim 12, wherein the reconstituted composition is administered when the subject is no longer intoxicated, but while the subject still has the hangover.

15. The method of claim 12, wherein the onion juiced powder comprises red onion and the leafy green vegetable juiced powder comprises romaine lettuce.

16. The method of claim 12, wherein the liquid is selected from the group consisting of water, juice, soup, and broth.

17. The method of claim 16, wherein the liquid is soup.

18. The method of claim 17, wherein the soup is chicken soup.

19. The method of claim 16, wherein the liquid is a broth.

20. The method of claim 19, wherein the broth is a chicken broth.

21. A method for manufacturing a composition for treating a hangover, comprising:
   a. juicing onions to form juiced onions;
   b. juicing cucumbers to form juiced cucumbers;
   c. juicing leafy green vegetables to form juiced leafy green vegetables; and
   d. drying the juiced onion, the juiced cucumber, and the juiced leafy green vegetable to form a vegetable juiced powder, wherein the vegetable juiced powder comprises onion juiced powder present in an amount of approximately 5 percent to approximately 30 percent of a total weight of the vegetable juiced powder; cucumber juiced powder present in an amount of approximately 15 percent to approximately 80 percent of the total weight of the vegetable juiced powder; and leafy green vegetable juiced powder present in an amount of approximately 15 percent to approximately 80 percent of the total weight of the vegetable juiced powder.

22. The method of claim 21, wherein the juiced onions, the juiced cucumbers, and the juiced leafy green vegetables are dried using a spray drying technique.

23. The method of claim 21, wherein the juiced onions, the juiced cucumbers, and the juiced leafy green vegetables are dried using a freeze drying technique.

24. The method of claim 21, wherein the juiced onions, the juiced cucumbers, and the juiced leafy green vegetables are dried using a vacuum drying technique.

25. The method of claim 21, wherein the juiced onions, the juiced cumbers, and the juiced leafy green vegetables are dried separately from each other, then combined to form the vegetable juiced powder.

26. The method of claim 21, wherein the juiced onions, the juiced cucumbers, and the juiced leafy green vegetables are mixed together then dried together to form the vegetable juiced powder.

* * * * *